United States Patent [19]
Obersat

[11] Patent Number: 4,773,859
[45] Date of Patent: * Sep. 27, 1988

[54] ATTACHMENT FOR COUPLING DETACHABLE AND PERMANENTLY INSTALLED COMPONENTS FOR DENTAL PROSTHESES TO EACH OTHER

[76] Inventor: Adam Obersat, Gärtnereistrasse 25, D-6750 Kaiserslautern, Fed. Rep. of Germany

[*] Notice: The portion of the term of this patent subsequent to May 2, 2003 has been disclaimed.

[21] Appl. No.: 857,123

[22] Filed: Apr. 29, 1986

Related U.S. Application Data

[63] Continuation-in-part of Ser. No. 655,025, Sep. 26, 1984, Pat. No. 4,586,902.

[30] Foreign Application Priority Data

Oct. 3, 1983 [DE] Fed. Rep. of Germany ....... 3335904
May 24, 1984 [DE] Fed. Rep. of Germany ....... 3419359

[51] Int. Cl.4 .............................................. A01C 13/22
[52] U.S. Cl. ..................................... 433/177; 433/181
[58] Field of Search ................ 433/177, 181, 182, 183

[56] References Cited

U.S. PATENT DOCUMENTS 1,863,230 6/1932 Shapiro .............................. 433/177
3,089,242 5/1963 Weissman ......................... 433/177

Primary Examiner—Robert Peshock
Attorney, Agent, or Firm—Peter K. Kontler

[57] ABSTRACT

The detachable component of a dental prosthesis is releasably secured to the permanently installed component by one or more pairs of male and female detent members. Each male detent member has a miniature flat brick-shaped compartment for a flat serpentine (particularly U-shaped or S-shaped) or a flat block-shaped spring whose front portion can bias or constitute a plunger which extends from the compartment and snaps into the respective female detent member. The male detent member or members are mounted on the detachable component and the female detent member or members are provided in or on the permanently installed component, preferably very close to the gum of the respective jaw. The casing which defines the compartment of the male detent member can be a prefabricated part or it may be formed, at least in part, during casting of the metallic part or parts of the detachable component. The overall dimensions of the male detent member need not exceed 5×3.5×1 mm.

23 Claims, 9 Drawing Sheets

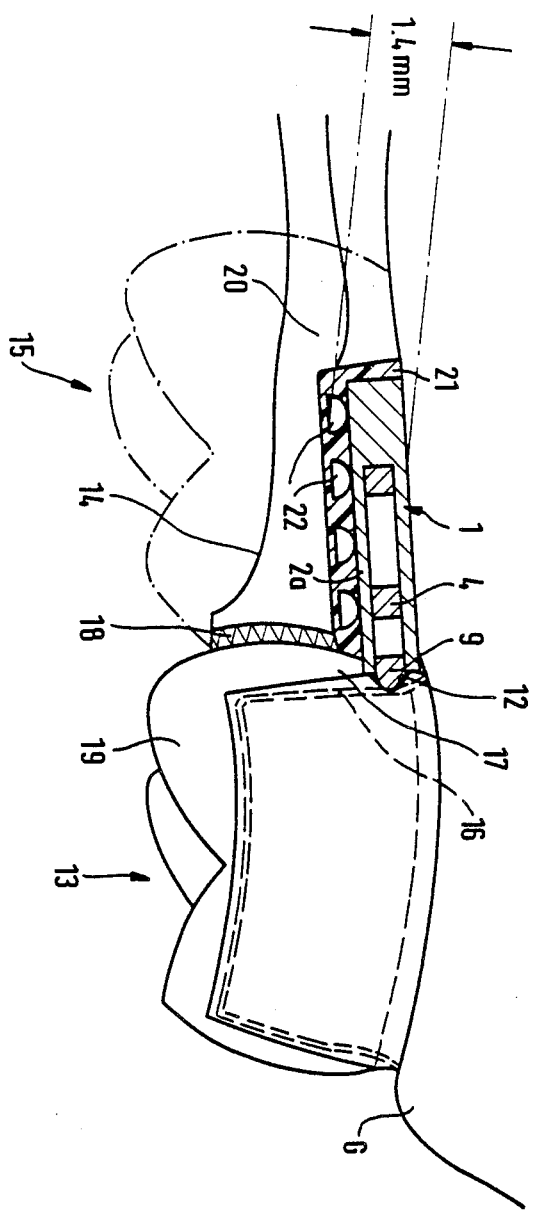

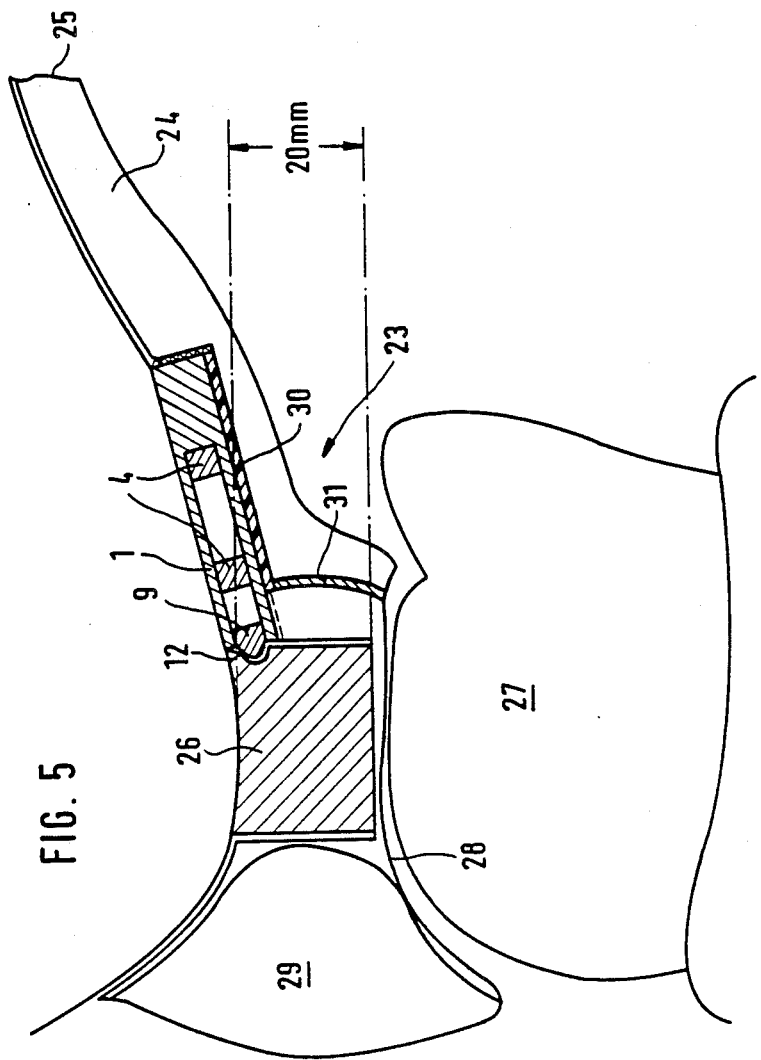

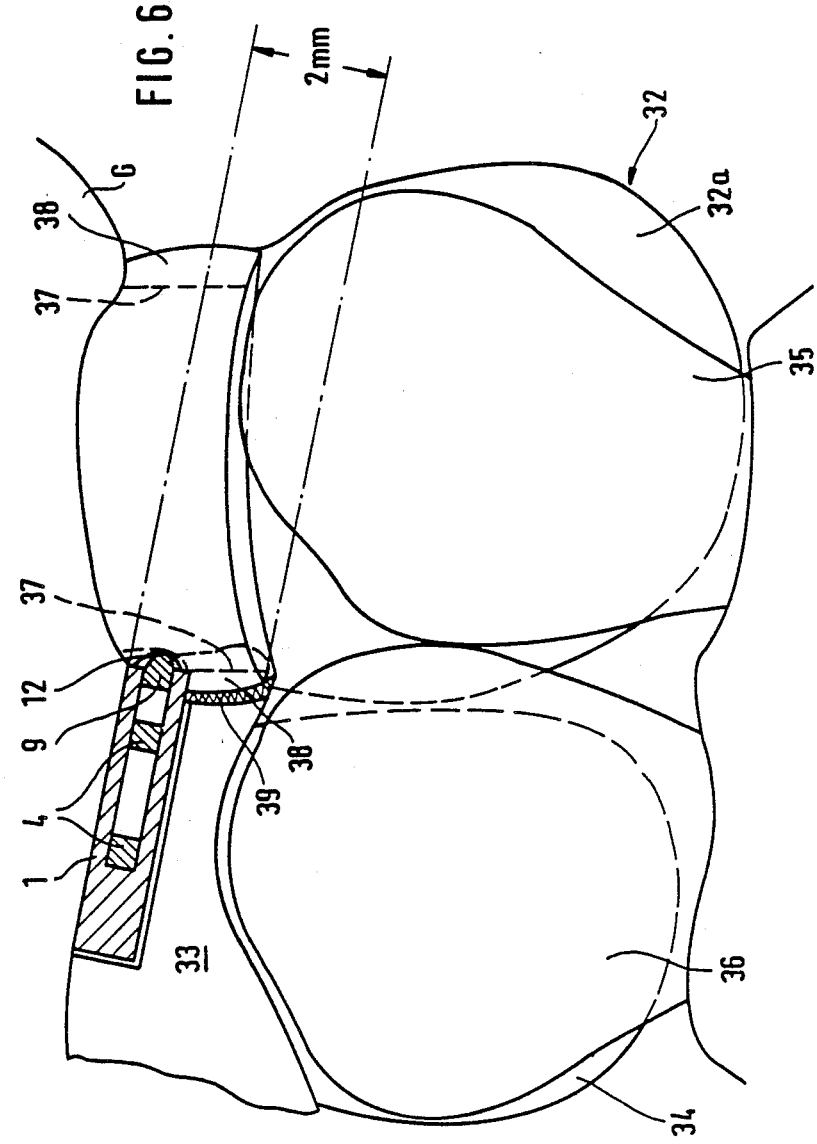

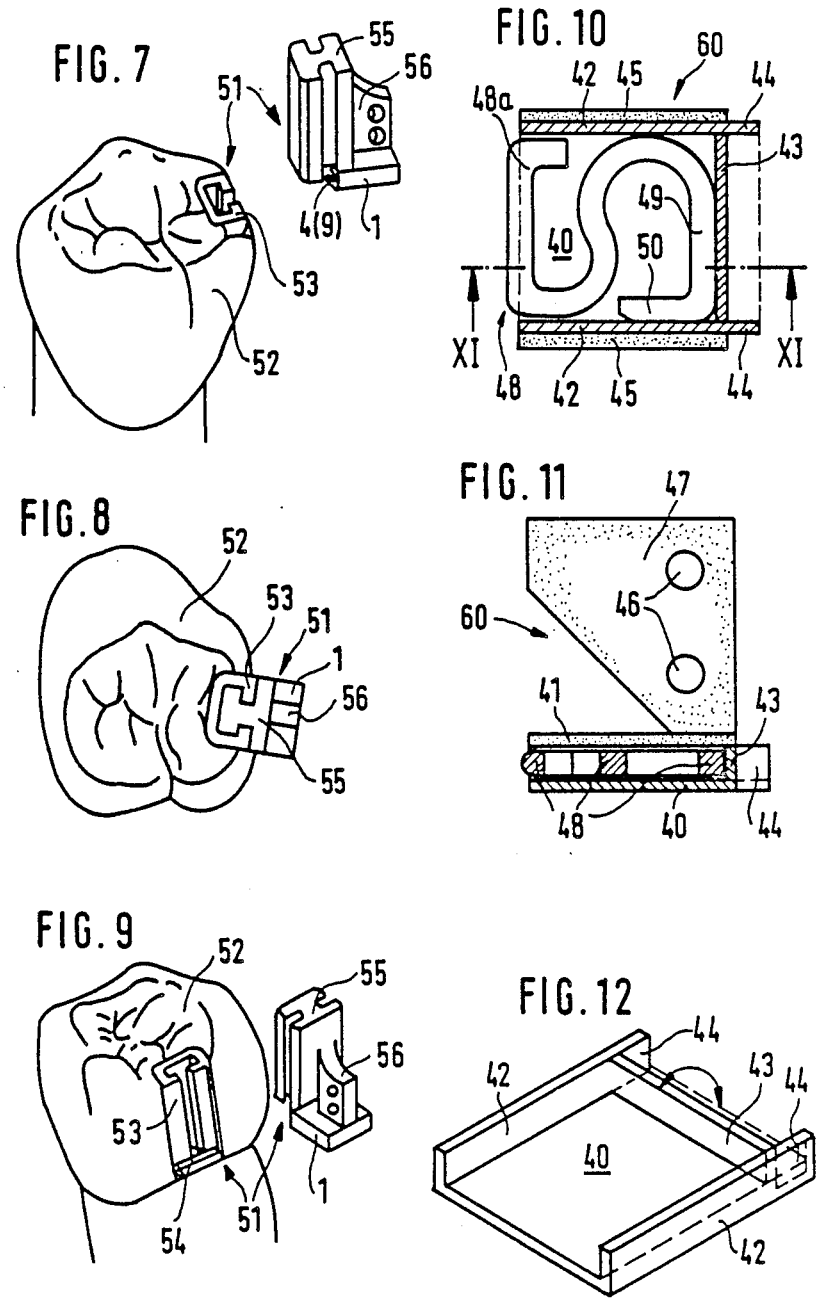

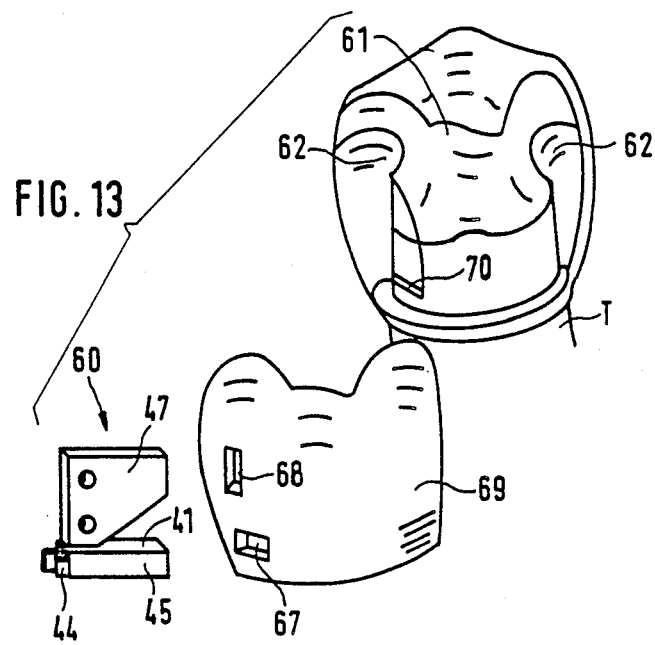
FIG. 13
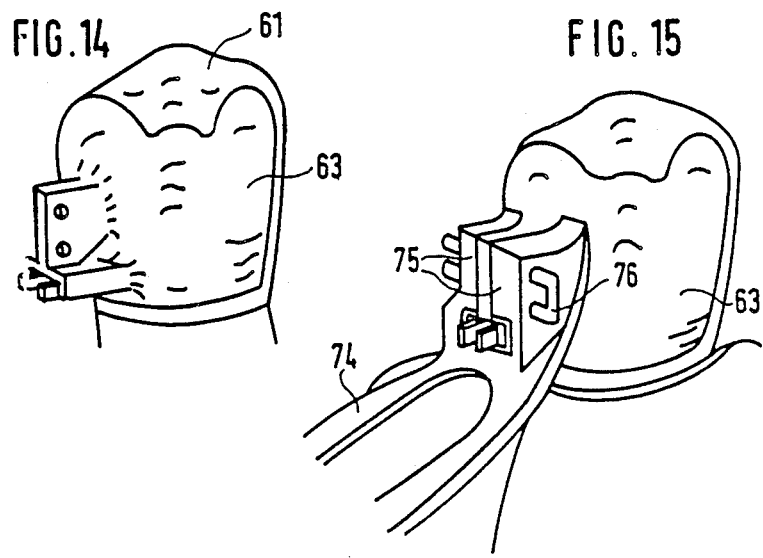
FIG. 14
FIG. 15

ATTACHMENT FOR COUPLING DETACHABLE AND PERMANENTLY INSTALLED COMPONENTS FOR DENTAL PROSTHESES TO EACH OTHER

CROSS-REFERENCE TO RELATED CASE

This is a continuation-in-part of my copending patent application Ser. No. 655,025 filed Sept. 26, 1984, now U.S. Pat. No. 4,586,902 granted May 6, 1986.

BACKGROUND OF THE INVENTION

The present invention relates to improvements in separable attachments between installed and removable components of dental prostheses. More particularly, the invention relates to improvements in so-called spring-loaded retention elements of the type wherein the female detent element is normally positioned below the survey line and the male detent element can snap into the female detent element by spring action. The invention also relates to a method of making the attachment and to improvements in means for facilitating the practice of the method.

In presently known attachments of the above outlined character, the male detent member comprises a flexible or bendable spring which is receivable in the recess of the female detent member (also known simply as female). The flattest conventional male detent member uses a spring which is made of wire having a diameter of 0.7 mm or thereabout, and such wire is inserted into a compartment with certain freedom of movement for penetration into or expulation from the recess of the female detent member. The overall thickness of the male detent member including the receptacle for the spring is in the range of 2 mm.

Certain other presently known attachments of the above outlined character comprise male detent members wherein a plunger is reciprocable under the action of a coil spring so that its head can penetrate into the recess of the female detent member. The minimum diameter of the plunger is 2.9 mm and the overall thickness of the male detent member is well in excess of the diameter of the plunger since the latter must be received, with a certain amount of play, in a suitable cylinder which is installed in the detachable or in the permanently installed component of the prosthesis. However, the overall dimensions of male detent members which employ reciprocable plungers are smaller than those of the male detent members employing the aforementioned bendable spring because the bendable spring occupies more room than the plunger and the coil spring therefor. Moreover, the bendable spring must be adequately anchored in the corresponding component of the prosthesis. Attempts to reduce the overall dimensions of male detent members which employ bendable springs have failed because a very small spring cannot be properly manipulated by the dental technician and also because the time which is required for proper installation of a very small spring would render the cost of the prosthesis employing two or more male detent members with miniature springs prohibitively high.

OBJECTS AND SUMMARY OF THE INVENTION

An object of the invention is to provide a novel and improved attachment which can be used to separably secure a detachable component of a dental prosthesis to the component which is permanently or more or less permanently installed in the mouth of the wearer.

Another object of the invention is to provide an attachment which can employ male and female detent members whose dimensions are a minute fraction of the dimensions of presently known male and female detent members but which is nevertheless capable of reliably holding the detachable component in proper position relative to the permanently installed component of the prosthesis.

A further object of the invention is to provide a novel and improved male detent member which can be used in an attachment of the above outlined character.

An additional object of the invention is to provide a male detent member whose thickness can be less than 1 mm and which can be installed in existing or in newly made components of dental prostheses in a surprisingly simple material- and time-saving manner.

Still another object of the invention is to provide a male detent member which need not necessarily employ a discrete plunger and wherein a novel spring can serve as a means for actually holding the male detent member in proper engagement with the female detent member.

An additional object of the invention is to provide a novel and improved method of making the male detent member and of installing such detent member in the corresponding component of the prosthesis.

Still another object of the invention is to provide novel and improved means for facilitating the practice of the just outlined method.

Another object of the invention is to provide a novel and improved dental prosthesis which embodies one or more detent members of the above outlined character.

A further object of the invention is to provide novel and improved detachable and/or permanently installed components of dental prostheses which embody detent members of the above outlined character.

One feature of the invention resides in the provision of an attachment between stationary (namely more or less permanently installed) and removable (e.g., bridge-like) components of a dental prosthesis. The attachment comprises a female detent member in or on one of the components (at the present time, the female detent member is preferably provided in or on the stationary component) and a male detent member which comprises a flat hollow casing provided in the other component and having an opening. The male detent member further comprises a flat serpentine (e.g., U-shaped or S-shaped) spring or a flat block-shaped spring which is installed in the casing, and a flat plunger which is biased by the spring to normally extend from the casing through the aforementioned opening and is receivable in the female detent member. The plunger can constitute or can be bonded to the front portion of the spring. The one component includes a portion which is adjacent to the gum of the respective jaw of the wearer of the prosthesis, and the female detent member is preferably provided in such portion of the one component, i.e., close to the gum.

The front portion of a serpentine spring is preferably straight or substantially straight and preferably extends only partially beyond the opening of the casing while it is received in the female detent member. The casing is preferably provided with a substantially rectangular flat compartment for the spring and, if the latter is a serpentine spring, it preferably comprises two additional portions which flank the front portion and are slidable along two spaced-apart parallel internal guide surfaces of the casing. The cross-sectional outline of the serpentine spring is preferably a polygon (most preferably a square or a rectangle) and the front portion of the serpentine spring preferably tapers in a direction away from the interior of the casing. Anchoring means (e.g., a projection on the spring and a complementary recess or hole in the casing) can be provided to secure the serpentine spring in the casing in such a way that the front portion of the serpentine spring is movable relative to the casing during insertion of the removable component into, or during removal of such component from, the mouth of the wearer. The maximum dimension of the cross section of the spring is preferably less than 0.7 mm, most preferably between 0.35 and 0.5 mm.

A block-shaped spring can be made of a rubber-like material (e.g., silicone rubber) and can substantially fill the compartment of the casing. The first end portion of such spring can be bonded to a separately produced metallic plunger.

In accordance with a presently preferred embodiment of the invention, the attachment can constitute a so-called friction grip slide attachment with a female part and a male part which latter is receivable in and is slidable relative to the female part. One of these parts is provided on the one component and the other part is provided on the other component. The detent members are provided on the corresponding parts and serve to releasably hold the male part against movement relative to the female part after the male part is properly inserted into the female part. The male and female parts are or can be made integral with the respective detent members.

Another feature of the invention resides in the provision of a method of making a separable attachment of the above outlined character, i.e., an attachment between stationary and separable or detachable components of a dental prosthesis wherein one of the components carries a female detent member and the other of the components carries a male detent member having a flat hollow casing with an opening and a serpentine or block-shaped spring installed in the casing and including a front portion which constitutes or carries a plunger that normally extends from the casing through the opening and is receivable in the female detent member. The method comprises the steps of making a pattern of the other component (e.g., a pattern which is made of wax or a casting resin), installing the pattern and the male detent member in a casting mold, evacuating the material of the pattern (e.g., by heating the mold) so as to leave in the mold a cavity for reception of flowable metallic material, introducing the metallic material into the cavity, and integrating the male detent member into the thus obtained other component. The casing is preferably made of a metallic material, and the method preferably further comprises the step of prefabricating at least a portion of the casing prior to the installing step. For example, the casing can be made of a single piece of metallic material or of two portions which are assembled to define a compartment for the spring. The casing and the other component preferably consist of alloys which are melted into each other in the course of the integrating step while the casing retains its shape to ensure that it can properly receive the spring. The method preferably further comprises the steps of inserting a prefabricated brick-shaped casting core into the casing prior to the installing step, removing the core from the casing upon completion of the integrating step, i.e., after the flowable metallic material of the other component is allowed to harden in the cavity of the mold, removing (e.g., extracting) the core from the interior of the casing upon completion of the integrating step, and installing the spring in the casing subsequent to such removing step.

A further feature of the invention resides in the provision of a combination of parts which can be used with advantage for the practice of the above outlined method. Such combination includes a flat block-shaped casting core and a casing having walls which surround at least four sides of the core (for example, at least one of the two smaller end faces of the flat brick-shaped core can remain exposed). The core is removable from the casing so that the latter can receive a spring a portion of which preferably constitutes a plunger that extends from the casing and is receivable in the female detent member. In accordance with one presently preferred embodiment, the casing comprises a substantially U-shaped first portion which surrounds three sides of the casting core and a second portion which forms with the first portion a flat tube and is adjacent to a fourth side of the core. The casing can be provided with a handle (e.g., a relatively large rib) and with at least one hole in the handle so that the latter can be attached to the frame of a bridge or the like.

Furthermore, the casing can comprise at least one extension (e.g., in the form of a lug which constitutes an integral part of the aforementioned U-shaped first portion) which is arranged to be embedded in forming sand in a casting mold wherein the casing is connected with the other component of the prosthesis. The casing is normally elongated and the aforementioned extension or extensions are preferably provided at one end of the elongated casing.

An additional feature of the invention resides in the provision of a kit for the making of a male detent member for use as a part of a separable attachment between stationary and removale components of a dental prosthesis wherein the male detent member is installed in one of the components and cooperates with a female detent member in the other component to separably couple the components to each other. In accordance with one presently preferred embodiment, the kit comprises a prefabricated flat hollow casing which defines the aforementioned flat compartment having a width greatly exceeding its height and is provided with an opening which communicates with the compartment, a flat spring (e.g., a serpentine metallic or plastic spring, a serpentine spring embedded in a soft mass of silicone rubber or the like, or a block-shaped spring of silicone rubber or the like) which is insertable into the compartment and has a width and a height respectively approximating the width and height of the compartment in the casing, and a plunger (which can be bonded to, made integral with or movable independently of the spring) which is arranged to be biased by the spring upon insertion of the spring and plunger into the compartment so that the plunger normally extends from the casing through the opening under the bias of the spring and can penetrate into the socket of a female detent member in a dental prosthesis. A common envelope can be provided for the casing, for the spring and for the plunger. Still further, such kit can comprise a prefabricated casting core which is used for the making of the casing and which can remain in the compartment of the casing during installation of the casing in one component of a dental prosthesis.

If the casing is to be formed around the casting core by the party who has purchased the kit, the latter can comprise only a prefabricated casting core and a prefabricated serpentine, block-shaped or other suitable spring (with a plunger bonded to the spring, with a plunger forming an integral part of the spring or with a plunger constituting a separate part).

If the casing is partly prefabricated, the kit can comprise one or more (e.g., U-shaped) casing portions which preferably partially or completely surround the casting core in the envelope of the kit. Such envelope is designed for joint shipment of prefabricated parts to a dental technician or to a dental laboratory.

The novel features which are considered as characteristic of the invention are set forth in particular in the appended claims. The improved attachment itself, however, both as to its construction and the mode of making and assembling the same, together with additional features and advantages thereof, will be best understood upon perusal of the following detailed description of certain specific embodiments with reference to the accompanying drawing.

BRIEF DESCRIPTION OF THE DRAWING

FIG. 4 is a fragmentary perspective partly sectional view of a dental prosthesis which employs the male detent member of FIGS. 1 to 3;

FIG. 5 is a fragmentary perspective partly sectional view of a different prosthesis which employs the male detent member of FIGS. 1 to 3;

FIG. 6 is a fragmentary partly sectional view of a third prosthesis which employs the male detent member of FIGS. 1 to 3;

FIG. 7 is a fragmentary perspective view of a fourth prosthesis which employs the male detent member of FIGS. 1 to 3, the male detent member being provided on a male part or connector which is detached from the complementary female part of connector;

FIG. 8 is a plan view of the structure which is shown in FIG. 7, with the male part inserted into the female part and with the male detent member engaging the female detent member;

FIG. 9 is a different perspective view of the structure which is shown in FIG. 7;

FIG. 10 is a sectional view of a modified male detent member whose casing has a handle or rib for connection to the frame of a bridge or another separable component of a dental prosthesis;

FIG. 11 is a sectional view as seen in the direction of arrows from the line XI—XI of FIG. 10;

FIG. 12 is a perspective view of the main or first portion of the casing of the male detent member which is shown in FIGS. 10 and 11;

FIG. 13 is an exploded perspective view of a permanently installed section of a crown which is provided with a female detent member and of a wax pattern which is about to be assembled with a male detent member of the type shown in FIGS. 10 and 11;

FIG. 14 illustrates the crown section of FIG. 13 and the finished detachable crown section which carries a male detent member of the type shown in FIGS. 10 and 11;

FIG. 15 illustrates the structure of FIG. 14 plus an additional portion of a bridge which includes the detachable crown section and the male detent member;

DESCRIPTION OF THE PREFERRED EMBODIMENTS

Figure 1:
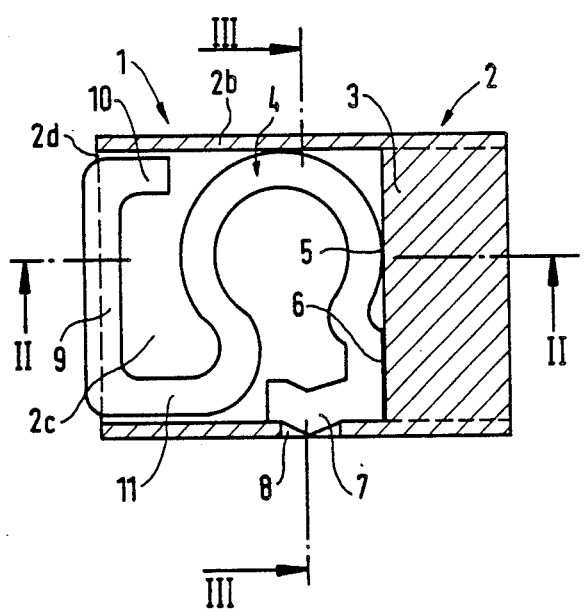
FIG. 1 is an enlarged sectional view of a male detent member which can be used in the improved attachment, the section being taken in the direction of arrows as seen from the line I—I of FIGS. 2 or 3.
Figure 3:
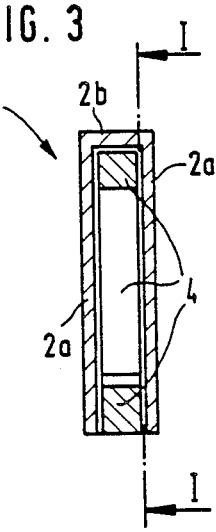
FIG. 3 is a sectional view of the male detent member as seen in the direction of arrows from the line III—III of FIG. 1.
Figure 2:
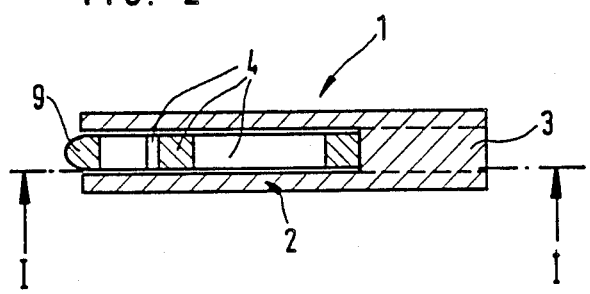
FIG. 2 is a sectional view of the male detent member as seen in the direction of arrows from the line II—II of FIG. 1.

Referring first to FIGS. 1 to 3, there is shown the male detent member 1 of an attachment which embodies one form of the invention. The male detent member 1 comprises a flat casing 2 which is made of an alloy that is customarily employed by dentists in connection with the making of prostheses. For example, the casing 2 can be made from a chromium-cobalt alloy or from an alloy which contains a noble metal. The casing 2 comprises a relatively thick solid block-shaped bottom wall 3, two spaced-apart flat parallel sidewalls 2a and two spaced-apart parallel end walls 2b. The walls 2a, 2b and 3 define a flat prismatic compartment 2c and the walls 2a, 2b define an opening 2d which is remote from and is located opposite the bottom wall 3. The casing 2 is an elongated flat brick-shaped body which can have the following dimensions: a thickness of 0.9 mm, a width of 3.5 mm and a length of 5 mm. The thickness of each of the sidewalls 2a and end walls 2b can be in the range of 0.2 mm.

The male detent member 1 further comprises a serpentine spring 4 which is installed in the compartment 2c and whose loops are disposed in a single plane, namely in a plane which is parallel to and is disposed between the planes of the sidewalls 2a. The spring 4 constitutes a length of suitably bent wire having a polygonal (preferably rectangular or square) cross-sectional outline (see FIG. 3). For example, the length of the sides of the square cross-section of the wire which constitutes the serpentine spring 4 can be in the range of 0.4 mm. Thus, the spring 4 is received in the compartment 2c with a play which is in the range of 0.1 mm (provided that the thickness of the casing 2 is 0.9 mm and the thickness of each sidewall 2a is 0.2 mm). The innermost portion of the spring 2 is configurated in such a way that it contacts the inner side of the bottom wall 3 at two spaced-apart locations 5 and 6. The illustrated serpentine spring 4 is a substantially S-shaped body and its confined end portion 7 has a lateral projection which is anchored in a hole 8 provided in the adjacent end wall 2b so that the spring is adequately anchored against accidental removal from the casing 2.

The outermost or front portion 9 of the spring 4 constitutes a plunger which normally extends in part from the casing 2, i.e., beyond the opening 2d and preferably constitutes a straight elongated element having a substantially V-shaped cross-sectional outline (see FIG. 2) so that it can more readily penetrate into the recess which is defined by the corresponding female detent member 12 (FIG. 4). That end portion (10) of the spring 4 which is remote from the bottom wall 2 is bent inwardly from the respective end of the front portion 9 and is slidably guided by the inner side of the respective end wall 2b. The end portion 10 cooperates with a further portion 11 of the spring 4 to ensure that the front portion 9 is adequately guided for movement toward and away from the bottom wall 3 without any or without appreciable changes in its orientation. The portion 11 is slidable along the inner side of the adjacent end wall 2b, namely along the inner side of that end wall which has the hole 8 for the projection of the end portion 7. The portions 10, 11 flank the front portion 9.

When the male detent member 1 is installed in the stationary or removable component of a dental prosthesis, preferably in the removable component such as the bridge 14 which is shown in FIG. 4, the front portion 9 is caused to penetrate into the compartment 2c while the bridge 14 is in the process of moving toward its inserted position and the front portion 9 is then permitted to move outwardly so that it penetrates directly into the recess or socket of the female detent member 12 which is provided in or on the stationary (installed) component of the prosthesis.

FIG. 4 shows a tooth 13 which carries a crown, and an artificial tooth 15 which is mounted on the bridge 14. When the bridge 14 is properly attached to the crown of the tooth 13, the latter is adjacent to the false tooth 15. The stump or stub 16 of the tooth 13 extends downwardly from the gum G and the crown of the tooth 13 comprises a frustoconical inner section 17 which surrounds the exposed part of the stub 16 and the major portion of which is, in turn, surrounded by an outer crown section 19 that resembles the exposed part of a tooth and is permanently secured to the cast metallic frame 20 of the bridge 14 by a layer 18 of solder. Thus, the inner crown section 17 constitutes the fixed or permanently installed component of the prosthesis and the outer crown 19 forms part of the removable component or bridge 14 of the prosthesis. The aforementioned casing 2 of the male detent member 1 is recessed into the metallic frame 20 of the bridge 14, and the space between its external surface and the surface bounding the recess in the frame 20 is filled with a mass 21 of suitable hardened synthetic plastic material. The outer side of one of the sidewalls 2a of the casing 2 can be provided with a set of anchoring elements 22 to further reduce the likelihood of accidental or unintentional separation of the casing 2 from the frame 20 of the bridge 14. The male detent member 1 can be mounted in an existing bridge 14 or it can be installed in the recess of the frame 20 during the making of the bridge.

The female detent member 12 forms part of the inner section 17 of the crown 17, 19 for the stub 16 of the tooth 13. When the bridge 14 is properly installed in the mouth of the wearer of the prosthesis, the inner crown section 17 depresses the front portion 9 of the spring 4 into the compartment 2c of the casing 2, at least during the last stage of insertion of the bridge, and the front portion 9 is thereupon caused to move outwardly due to innate resiliency of the spring 4 and penetrates into the recess or socket of the female detent member 12 to ensure adequate retention of the bridge in the mouth. At such time, the outer crown section 19 (which is an integral part of the bridge 14) overlies and conceals the inner crown section 17 on the stub 16 of the tooth 13. The bias of the spring 4 (i.e., the resistance of the spring 4 to deformation which involves penetration of the entire front portion 9 (or of the major part of the front portion 9) into the compartment 2c of the casing 2) is selected with a view to prevent accidental detachment of the male detent member 1 from the female detent member 12, i.e., to ensure that the wearer of the bridge 14 must exert a reasonable force in order to push the front portion 9 back into the compartment 2c in order to detach the male detent member 1 from the female detent member 12. The layer 18 of solder is relatively large and is adjacent to a portion of the mass 21 of hardened synthetic plastic material in the recess of the frame 20.

An important advantage of the improved male detent member 1 is that it constitutes a prefabricated product which can be readily incorporated in the corresponding component of the prosthesis (as a rule, the male detent member will be installed in the detachable component because it can be readily inspected whenever the detachable component is removed from the mouth of the wearer; however, it is equally possible to provide the detent member 1 in or on the permanently installed component of the prosthesis). Another important advantage of the detent member 1 is that it is extremely small but is nevertheless capable of cooperating with the female detent member 12 to adequately hold the detachable component of the prosthesis in proper position with reference to the permanently installed component. The serpentine spring 4 takes up a very small amount of space so that the casing 2 can be formed with a flat compartment 2c whose height (between the sidewalls 2a) need not appreciably exceed the maximum dimension of the cross section of the spring 4. Such serpentine springs can be mass produced in any desired size and/or shape at a very low cost, and their insertion into the respective compartments 2c presents no problems. Adequate anchoring of an inserted spring 4 is ensured by the aforementioned anchoring means 7, 8 or by analogous or other suitable anchoring means. All a technician has to do is introduce the proper end of the spring 4 into the compartment 2c by way of the opening 2d to such an extent that the projection 7 snaps into the hole 8 whereby the spring is properly anchored in the casing 2 and its front portion 9 extends partly through and outwardly beyond the opening 2d. The feature that the front portion 9 tapers in a direction away from the interior of the casing 2 facilitates the introduction of such front portion into the female detent member as well as extraction of the front portion from the female detent member 12 when the wearer or a dentist desires to extract the component 14 from the wearer's mouth. It has been found that, in spite of its miniature size, the improved male detent member 1 can cooperate with the female detent member 12 to properly hold a detachable component (such as 14) which had to be provided with unsightly and bulky clamps if it was to be properly inserted in accordance with heretofore known techniques.

Another important advantage of the male detent member 1 is that its casing 2 is not only extremely flat but also that the width and the length of the casing are surprisingly small. Thus, a serpentine spring 4 of adequate strength can be readily accommodated in a very small compartment 2c and is adequately guided therein because the spring portions 10, 11 which flank the front portion 9 are slidable along the adjacent internal surfaces of the parallel end walls 2c of the casing 2. The feature that the spring 4 can be installed in a casing 2 whose width and length are also small or extremely small is highly desirable in many types of prostheses because the detent member 1 must be installed in that portion of the component 14 or another detachable component which is subjected to maximum stresses when the prosthesis is in use. The just mentioned portion of the component 14 is that portion which is separably coupled to the component 17 by way of the detent members 1 and 12.

The feature that only a part of the front portion 9 of the spring 4 extends from the casing 2 when such front portion is received in the recess of the female detent member 12 or when the component 14 is detached from the component 17 is desirable and advantageous because the confined part of the front portion 9 at least substantially seals the opening 2d and thus prevents penetration of foreign matter into the compartment 2c. Moreover, such mounting of the spring 4 enhances its ability to stand pronounced stresses and to reliably hold the component 14 in place except when the wearer or the dentist desires to detach the component 14 from the component 17. The utilization of a spring having a polygonal (preferably square or rectangular) cross-sectional outline is desirable and advantageous because such spring is in large surface-to-surface contact with and is adequately guided by the casing 2. Moreover, such a spring (and more particularly its front portion 9) is more likely to adequately seal the opening 2d to thus prevent penetration of foreign matter into the compartment 2c. Still further, the maximum transverse dimension of the square or substantially square cross section of a wire is less than the diameter of a round wire having the same cross-sectional area. As mentioned above, the maximum dimension of the cross-section of the spring 4 need not exceed 0.7 mm and is preferably between 0.35 and 0.5 mm.

FIG. 5 shows the manner in which the male detent member 1 is installed in a different detachable or removable component 23 of a dental prosthesis. The connecting yoke 24 between the illustrated half of the detachable component 23 and the other half (which also carries a male detent member 1) is broken away, as at 25. The front portion 9 of the spring 4 in the casing 2 of the male detent member 1 shown in FIG. 5 extends into the recess of a female detent member 12 forming part of a solid beam 26 which is rigidly connected to the crowns of two spaced-apart teeth, one in front of and the other behind the plane of FIG. 5. The reference character 27 denotes a tooth in the lower jaw of the wearer of the prosthesis. The beam 26 forms part of the permanently installed component, and the structure 23 is the removable or detachable component of the prosthesis. A surface 28 at the underside of the properly inserted component 23 is located opposite the top surface of the tooth 27. The exposed front side of the component 23 carries a facing or liner 29 which is made of a ceramic or synthetic plastic material and constitutes a false tooth.

The manner in which the casing 2 of the male detent member 1 is installed in the detachable component 23 of the prosthesis is analogous to that which was described with reference to FIG. 4. Thus, the yoke 24 of the component 23 has a recess which is large enough to receive the casing 2 with some room for a mass 30 of hardened synthetic plastic material or solder which ensures adequate retention of the casing 2 in the yoke 24 under all foreseeable circumstances. As mentioned above, the female detent member 12 is provided on the beam 24 of the fixedly installed component of the prosthesis and its recess receives the front portion 9 of the serpentine spring 4 in the compartment 2c of the casing 2 when the component 23 is properly inserted. The reference character 31 denotes a layer of solder which connects the yoke 24 of the component 23 with the facing or liner 29. Due to its rather insignificant thickness, the entire casing 2 of the male detent member 1 can be fully recessed into the yoke 24 without undue weakening of the corresponding portion of the detachable component 23. In fact, the illustrated casing 2 is recessed into the yoke 24 at a level above the layer 31 of solder or hardened synthetic plastic material. The height of the illustrated beam 26 is in the range of 2 mm. If desired, the casing 2 can constitute an integral part of the casting which is the yoke 24 so that the mass 30 can be omitted.

FIG. 6 shows a crowned tooth 32 in the mouth of the wearer and a false tooth 34 which is provided on the removable or detachable component 33 of the prosthesis. The teeth 32 and 34 are adjacent to each other. The tooth 32 extends downwardly from the upper jaw and the teeth 32, 34 are located in front of two teeth 35, 36 in the lower jaw. The inclined front sides of the teeth 35, 36 are adjacent to the complementary rear sides of the teeth 32, 34 when the wearer's mouth is closed. This provides very little room for the removable component 33 of the prosthesis, i.e., for the component which, in the embodiment of FIG. 6, carries the male detent member 1 and includes a cast metallic frame.

The drowned tooth 32 includes an exposed and visible outer crown section 32a which is located in front of the tooth 35 and whose uppermost part 38 surrounds and is removably mounted on the inner crown section 37 surrounding the stub of the respective tooth in the upper jaw. The section 32a forms part of the removable component 33 of the prosthesis. The female detent member 12 is provided on the inner crown section 37 which constitutes or forms part of the permanently installed component of the prosthesis. The casing 2 of the male detent member 1 is recessed into the metallic frame of the removable component 33. A layer 39 of solder is provided to connect the metallic frame of the component 33 with the portion 38 of the outer crown section 32a.

The structure which is shown in FIG. 6 is a typical example of a prosthesis whose removable component 33 could not be adequately and reliably installed in the mouth without resorting to clamps or the like were it not for the extremely small and flat male detent member 1 which renders it possible to provide the complementary female detent member 12 on the inner section 37 of the crown for the tooth 32 in immediate proximity of the gum G.

FIGS. 7 to 9 illustrate the manner in which the improved male and female detent members can be installed in a prosthesis wherein the attachment 51 between the permanently installed and detachable components of the prosthesis is a so-called friction grip slide attachment with a female part 53 embedded in the crown 52 of a tooth extending from the lower jaw of the wearer and a complementary male part 55 installed on the detachable component (not shown) of the prosthesis. The lowermost portion of the female part 53 includes a female detent member 54 (FIG. 9) and the corresponding portion of the male part 55 includes a male detent member 1 of the type shown in FIGS. 1 to 3. The housing 2 of the male detent member 1 is integral with the male part 55 of the attachment 51. The male part 55 further comprises a handle or rib 56 having two holes for fasteners which secure the part 55 to the detachable component of the prosthesis, e.g., to the cast metallic frame of a bridge. FIG. 7 shows the attachment 51 prior to insertion of the T-shaped rail of the male part 55 into the complementary slot of the female part 53. In FIG. 8, the parts 53 and 55 are assembled and the front portion 9 of the serpentine spring 4 in the casing 2 of the male detent member 1 is assumed to extend into the recess of the female detent member 54 on or in the female part 53 of the attachment 51 so as to hold the part 55 against movement relative to the part 53.

An important advantage of the structure which is shown in FIGS. 7 to 9 is that the length of the male and female parts 55, 53 can be reduced to a fraction of the length of similar parts in conventional attachments. This is due to the fact that the miniature male detent member 1 suffices to ensure reliable retention of a relatively short male part 55 in an equally short female part 53. The parts 53, 55 are or can be prefabricated, and they can be readily assembled with the corresponding detent members. Thus, the female detent member 54 can be formed by providing the corresponding portion of the female part 53 with a suitable notch or groove, and the casing of the male detent member 1 can constitute an integral part of the respective end portion of the male part 55.

FIGS. 10 to 12 illustrate a different male detent member which has a modified casing including a U-shaped first or main section 40 and a U-shaped second section 41 constituting a baked cover or lid which can consist of a pattern making material. As can be seen in FIG. 12, the main section 40 is made of a sheet or blank of metal by bending the sidewalls 42 and a bottom wall 43 from the general plane of the remainder of the blank. The extensions or lugs 44 of the sidewalls 42 extend rearwardly beyond the bottom wall 43. The width of the sidewalls 42 is the same as that of the bottom wall 43 so that each of the extensions 44 has a substantially square outline. The U-shaped cover or lid 41 has two sidewalls or cheeks 45 which overlie the outer sides of the sidewalls 42 of the main portion 40. The central portion of the cover 41 has an outwardly extending handle or rib 47 with two circular holes 46 for attachment to the removable component of the prosthesis. The rib 47 has a substantially triangular shape and is integral with the remainder of the cover 41 in the region of the bottom wall 43. The material of the rib 47 is preferably the same as that of the cover 41.

The serpentine spring 48 in the flat compartment of the casing including the main portion 40 and cover 41 is substantially identical with the spring 4 of the male detent member 1 shown in FIGS. 1 to 3. This spring has a substantially square cross-sectional outline and its confined end portion may but need not have a projection such as the projection of the end portion 7 shown in FIG. 1. The innermost portion 49 of the spring 48 is straight and abuts against the inner side of the bottom wall 43. The concealed inner end portion 50 is also straight and abuts against the inner side of the respective sidewall 42. It will be noted that the spring 48 is not positively anchored in the compartment of the casing including the main portion 40 and the cover 41. This renders it possible to readily insert such spring after the casing 40, 41 is already integrally connected to the respective component of the prosthesis. At the time the casing 40, 41 is being attached to the corresponding component of the prosthesis, the compartment within the casing is filled by a casting core 77 (FIG. 18) which, together with the casing 40, 41, constitutes a pattern 60 adapted to be used in a manner as shown in FIG. 13. The core 77 completely fills the compartment which is defined by the portions 40 and 41 of the casing. FIG. 13 shows a crown section 61 which forms part of the fixedly installed component of the prosthesis. The crown section 61 is formed with two tapering grooves 62 for two complementary tapering male parts on a second crown section 63 (FIGS. 14 and 15). The opening 67 in a wax pattern 69 (FIG. 13) of the crown section 63 serves to receive a portion of the casing including the portions 40, 41, and the hole 68 of the pattern 69 serves to receive a portion of the handle or rib 47. The sections 61 and 63 together constitute a complete crown for the stub or stump of a tooth T. In order to make the detachable crown section 63 of a suitable metallic alloy, it is necessary to make the pattern 69 of wax or another material which can be removed by heating, and such pattern 69 is then embedded in a casting mold 65 containing molding sand 66 or another heat- and fire-resistant material (see FIGS. 16 and 17).

The manner in which the pattern 69 is assembled with the element 60 is shown in FIG. 13. The pattern 69 is made by hand and is then assembled with the element 60. The openings or holes 67, 68 respectively receive portions of the casing 40, 41 and rib or handle 47. The mode of insertion is such that the open end of the compartment in the casing 40, 41 (actually, the compartment is filled by the aforementioned core) is leading during insertion into the opening 67 of the handmade pattern 69 and that the narrower upper portion of the handle or rib 47 is leading during insertion into the opening 68. The openings 67, 68 are completely filled when the element 60 is properly assembled with the hand-made pattern 69. The areas where the exposed surface of the pattern 69 surrounds the outwardly extending portions of the rib 47 and the casing 40, 41 are thereupon smoothed by addition of wax in a manner as shown in FIG. 14. Such added material strengthens the connection between the element 60 and pattern 69. FIG. 13 further shows that the open end of the compartment in the casing 40, 41 of the element 60 will be located directly in front of a recess or notch 70 (female detent member) which is machined into the external surface of the crown section 61 adjacent to the gum. When the core is removed and the compartment of the casing 40, 41 receives a serpentine spring 48 (which is shown in FIG. 10 only for the sake of clarity), the straight front portion 48a or plunger of such spring is free to extend into the recess 70.

Figure 16:
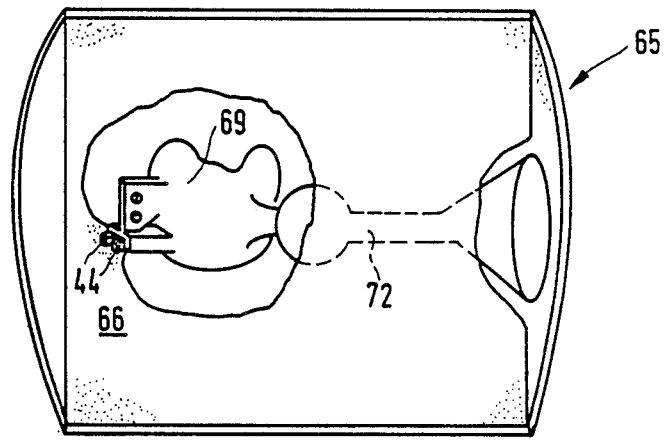
FIG. 16 is a schematic view of a casting mold for the making of the detachable crown section of FIGS. 14–15 and for permanent incorporation of a male detent member thereinto.
Figure 17:
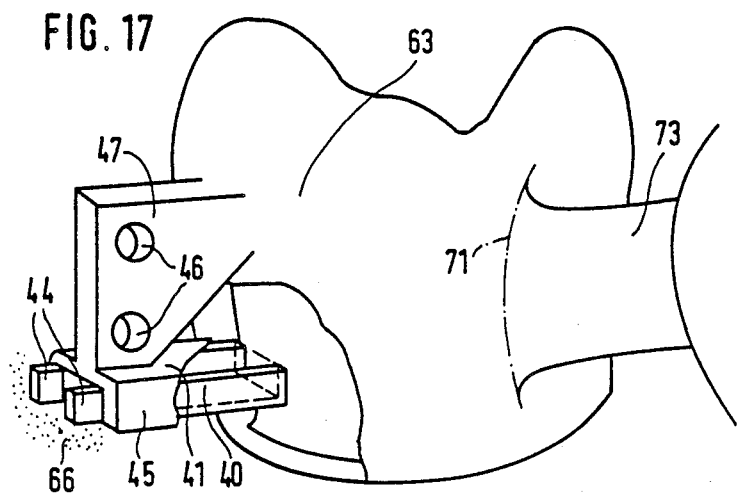
FIG. 17 is an enlarged perspective view of the detachable crown section and of the male detent member upon removal from the mold of FIG. 16.

FIG. 16 shows the composite pattern (including the element 60 and the wax pattern 69) in the casting mold 65 with some of the sand 66 removed in the region immediately around the pattern 69 for the sake of better visualization of the position of inserted parts. It can be seen that the extensions 44 of the two sidewalls 42 of the main portion 40 are embedded in the sand 66. The element 60 is held in proper position in the mold 65 only as a result of the end portions 44 being embedded in the sand 66 after the material (e.g., wax) of the pattern 69 is removed from the mold 65 as a result of heating so that the resulting cavity can be filled with a molten alloy which is to form part of the removable component of the prosthesis. The specific weight of the core which fills the cavity of the casing 40, 41 in the mold 65 is less than the specific weight of molten alloy so that, if the extensions 44 were not embedded in the sand 66, the element 60 would become detached from the sand and would float in the introduced liquid metallic material. Anchoring of element 60 in the mold 65 must be reliable and accurate because the major portions of the cheeks 45 and the exposed part of the portion 40 should be completely surrounded by the introduced metallic material in order to ensure that the male detent member will constitute an integral part of the detachable component of the prosthesis. In other words, the casting which is obtained upon cooling of introduced molten metallic alloy includes the element 60 as an integral part. The channel for introduction of molten alloy is shown at 72 (see FIG. 16). When the cavity which is obtained upon melting of the material of the pattern 69 is filled with liquid metallic material and such material is thereupon allowed to set, the projecting metallic portion 73 (surplus) which extends beyond the phantom line 71 of FIG. 17 is removed by severing or in any other suitable way.

FIG. 14 shows the finished separable crown section 63 which is assembled with the installed crown section 61 of FIG. 13. The section 63 is attached to the section 61 in that its tapering male portions extend into the complementary tapering grooves 62 of the section 61. The sections 61 and 63 are firmly but nevertheless separably held together by the male and female detent members 60 and 70 in that the straight front portion or plunger 48a of the spring 48 in the compartment of the casing 40, 41 (such compartment receives the spring 48 upon removal of the core 77) extends into the recess 70 in the fixedly installed crown section 61. The holes 46 in the exposed portion of the handle or rib 47 serve to receive fastener means (e.g., a U-shaped fastener 76 shown in FIG. 15) which secures the rib 47 to the frame 74 of a yoke or another part of the detachable component of the prosthesis. The frame 74 can support one or more false teeth, not shown. The exposed portion of the rib 47 is received between two plate-like protuberances 75 of the frame 74, and such protuberances are provided with openings registering with the openings 46 of the rib 47 so as to allow for the passage of legs forming part of the U-shaped fastener 76. The latter can consist of metallic wire and is more or less permanently secured to the rib 47 and protuberances 75 in a manner which is not specifically shown in the drawing. The connection between the frame 74 and the rib 47 is preferably concealed (at least in part) by a false tooth (not shown) on the frame 74.

If the removable component of the prosthesis including the structure of FIG. 15 is to be detached from the permanently installed component (crown section 61), the wearer or a dentist exerts upon the removable component a pull in an upward direction, as viewed in FIG. 15, so that the front portion 48a of the spring 48 is extracted from the recess 70.

Figure 18:
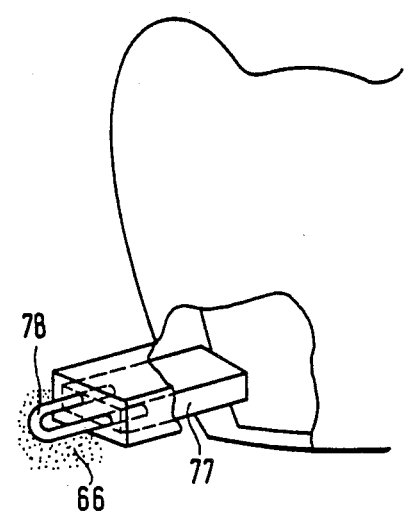
FIG. 18 is a fragmentary perspective view of a crown section and of a male detent member which is somewhat similar to the male detent member of FIGS. 1 to 3.

FIG. 18 shows the casting core 77 in the compartment of a casing which is similar to the casing 2. The core 77 comprises a U-shaped handle 78 which is accessible for engagement with a tool to facilitate extraction of the core 77 from its compartment upon completion of the work which is involved in the making of the detachable component of the prosthesis. Cores of the type shown in FIG. 18 can be used by dental technicians for the making of the entire removable component solely by hand, i.e., without making a wax pattern and without resorting to the mold 65 of FIG. 16. When the core 77 is removed, the compartment of the casing of the male detent member is ready to receive a serpentine spring, such as the spring 48 of FIG. 10. Of course, the core 77 can also be used in connection with the making of a detachable component in a manner as described in connection with FIGS. 16 and 17.

The provision of the casting core 77 is advisable and advantageous because, at least in many instances, the male detent member 1 but especially that which is shown in FIG. 14 will be incorporated into a cast metallic part of the detachable component of a dental prosthesis. Such casting core is a prefabricated part which can be mass-produced at a reasonable cost and can be readily manipulated by a dental technician, even if it is not provided with the handle 78.

The prefabricating procedure can be extended beyond the mere making of prefabricated cores 77. Thus, and as described in connection with FIGS. 10 to 12, the casing of the male detent member can be made of prefabricated portions 40, 41 which together form a tubular body (with one end closed by the end wall 43) and surround at least four sides of a properly inserted core 77. The alloy of the casing is preferably compatible with the alloy which is poured into the cavity of the casting mold 65 upon removal of the material of the pattern 69 so that the male detent member is fully integrated into the detachable component 63. During integration, the core 77 ensures that the configuration of the compartment in the casing remains unchanged so that the compartment can properly receive the spring 4 or 48. As a rule, the male and female detent members will be located in immediate or very close proximity of the respective gum G when the two components of the prosthesis are properly attached to each other, i.e., when the male detent member engages the associated female detent member. This not only results in concealment of the detent members but also ensures that the relatively thin male detent member can properly retain the detachable component in an optimum position in the region where the detachable component receives and transmits stresses of maximum magnitude. As can be seen in each of FIGS. 4-6, a portion of the casing of the male detent member can remain exposed so as to constitute a visible part of the detachable component. This is desirable on the ground because the technician can readily inspect the detachable component for the purpose of ascertaining whether or not the casing is properly embedded in the cast metallic frame of such component, i.e., the technician can more readily detect the presence or absence of casting defects. As a rule, the likelihood of the presence of casting defects is rather pronounced when the thickness of the walls of the casing is minimal. This holds especially true if at least a portion of the casing of the male detent member is formed simultaneously with the metallic frame of the detachable component of the prosthesis. If the casing merely comprises the U-shaped member 40 of FIGS. 10 to 12 and the wall which is formed by the central panel (between the cheeks 45) of the portion 41 is made during casting of the component 63, the overall thickness of the casing of the finished male detent member is reduced still further since the casing merely includes the portion 41 whose sidewalls 42 and bottom wall 43 are integral with the metallic body or frame of the detachable component.

A prefabricated casing (such as the casing 2 of the male detent member 1 shown in FIGS. 1 to 3) can be used with particular advantage for soldering or otherwise bonding to the prefabricated frame by a detachable component. Such prefabricated casing is preferably closed at all sides except in the region (opening 2d of the casing 2) where the plunger (e.g., the integral front portion 9 of the spring 4) is to extend from the casing and into the female detent member. The entire male detent member 1 can be prefabricated (including insertion of the spring 4 into the casing 2) and is then attached to the separable component of the prosthesis. This obviates the need for a core during attachment of the male detent member 1 to the frame of the detachable component.

The mode of assembling the male detent member with the detachable component as shown in FIGS. 10 to 18 is preferred at this time. Thus, the partially or completely prefabricated casing of the male detent member confines a removable casting core 77 and this detent member is then integrated into the respective component of the prosthesis during the making of the component. Such mode of making a complete detachable component allows for extensive automation and eliminates the need for manual work or reduces the extent of manual treatment of the detachable component to a minimum. It would be particularly tedious to manually close the casing including only the U-shaped portion 40 of FIG. 12 so as to ensure that the casing surrounds four sides of the core.

The exposed portion of the handle or rib 47 on the component 63 of FIG. 17 can be removed if it is not needed for connection to the frame 74 of FIG. 15 or to a like part. The handle 47 is preferably small and narrow; nevertheless, it facilitates proper manipulation of the element 60 which is to constitute or which is to facilitate the making of the male detent member in or on the finished component 63. The handle 47 can be made of a material which melts during the making of the component 63, or of a material whose consistency remains unchanged during melting and evacuation of the material of the pattern 69.

If the core 77 is inserted into a pattern resembling a finished male detent member of the type shown in FIG. 17, it is preferably provided with one or more anchors which are made of wire or the like and are embedded in the forming sand 66 in lieu of the extensions 44 so that the core 77 does not begin to float when the material of the pattern of the casing of the male detent member melts away and is evacuated from the mold 65 in order to provide a cavity which is then filled with a metallic alloy to form the casing of the male detent member on the thus obtained detachable component. The extensions 44 serve to adequately locate the core 77 in the mold 65 only if the portion 40 retains its shape during the making of the component 63, i.e., if the portion 40 constitutes a constituent of the casing of the male detent member on or in the finished component 63. The provision of anchoring means in the form of extensions 44 is desirable and advantageous if the portion 40 is to form part of the finished component 63 because the extensions 44 are present anyway when a sheet metal blank is converted into a U-shaped body 40 having two sidewalls 42 and a bottom wall 43.

If the attachment is to be used as a means which holds the detachable component exclusively by friction, it is preferably employed primarily in resiliently mounted telescopic bridges.

Figure 19:
FIG. 19 is a sectional view of a modified spring which is bonded to a separately produced plunger.

FIG. 19 shows a portion of a modified male detent member wherein a substantially block-shaped spring 204 is bonded to a metallic plunger 209. The spring 204 can be made of soft silicone rubber or another suitable synthetic plastic material and replaces the serpentine spring. When in use, the spring 204 substantially fills the flat compartment of the casing, such as the compartment 2c of the casing 2 which is shown in FIGS. 1 to 3. An advantage of the spring 204 is that its cost is a small fraction of the cost of a metallic or plastic serpentine spring, and also that it can be anchored (if necessary) in the casing in a simple and inexpensive manner, e.g., with a drop of adhesive. Bonding of the spring 204 to the metallic plunger 209 can be carried out in available machines. A plastic plunger can be used with equal or similar advantage.

The spring 204 can also be made of natural rubber. All that counts is to ensure that the spring 204 nearly completely fills the compartment of the casing for the aforediscussed purposes. Complete filling of the compartment by the spring 204 is not possible because, not unlike a liquid, the material of the spring 204 is not compressible. A very small clearance between the internal surface of the casing and the external surface of the spring 204 suffices to enable the spring to perform its dual function of biasing the plunger and of nearly completely filling the compartment. The plunger 209 need not necessarily be bonded to or partially embedded in the material of the spring 204; it often suffices to use a cap-like plunger which remains a separate part after installation in the casing.

Figure 20:
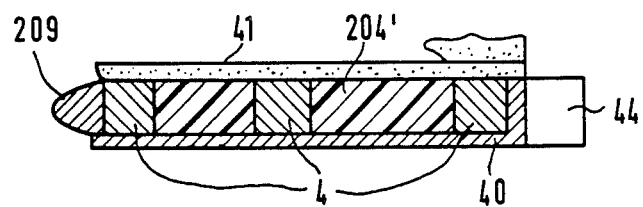
FIG. 20 is a sectional view of a further spring.

FIG. 20 shows a portion of a further male detent member wherein a substantially block-shaped mass 204' is adjacent to the rear side of a metallic plunger 209. The mass 204' can be made of soft silicone rubber or another suitable synthetic plastic material and is used with a serpentine spring 4. When in use, the spring 4 and the mass 204' at least substantially fill the compartment of the casing. The latter can be identical with the casing 2 of FIGS. 1–3 or with the casing 40, 41 of FIGS. 10–12. An advantage of the mass 204' is that it can practically completely fill that portion of the compartment in the casing which is not occupied by the serpentine spring. This greatly reduces the likelihood of growth of bacteria in the interior of the casing.

The mass 204' need not transmit and/or store any forces because all necessary forces are stored and transmitted by the serpentine spring 4. In this embodiment of the male detent member, the sole purpose of the mass 204' is to nearly completely fill the compartment of the casing.

Figure 21:
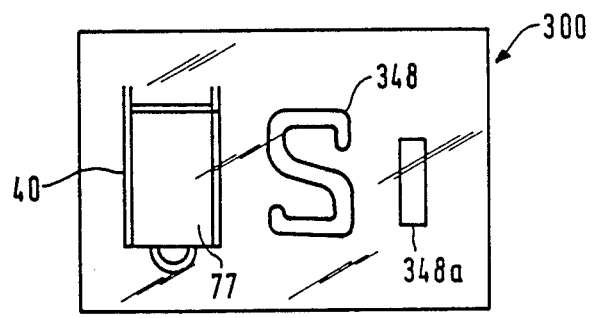
FIG. 21 is a schematic elevational view of a kit with a prefabricated casting core and other parts which can reduce the amount of manual work in connection with the making of a male detent member and its installation in a component of a dental prosthesis.

FIG. 21 shows one presently preferred kit for shipment of prefabricated components of the dental prosthesis from the manufacturer or distributor to customers, e.g., to dental laboratories or to individual technicians. The reference character 300 denotes schematically an envelope (e.g., a box, a bag or another suitable container) for a casting core 77 which may be of the type shown in FIG. 18, a portion 40 of a composite casing (such as the portion of FIG. 12) which partially surrounds the core 77 in order to reduce the overall dimensions of the kit, a prefabricated plunger 348a, and a prefabricated spring 348 which resembles the spring 48 of FIG. 10 except that it is not integral with the plunger 348a. It is clear that the spring 348 can be replaced with the spring 204 of FIG. 19 or with the spring 4, 204' of FIG. 20 and that the plunger 348a can be replaced with the plunger 209 of FIG. 19 or 20. If furnished as an element of the kit of FIG. 20, the plunger 209 may but need not be already bonded to the spring 204 or 4, 204'. It is equally possible to furnish the kit of FIG. 20 with a prefabricated portion 41 or with prefabricated portions 40, 41. Still further, the kit can be furnished only with a casting core and with a spring (which may be integral with the plunger) or with a core, a spring and a discrete plunger. Still further, the kit can include a complete casing which still contains a casting core and a spring having an integral plunger, or a casing containing a core, a spring and a discrete plunger. The furnishing of a prefabricated casing with a casting core therein is desirable and advantageous if the casing is to be embedded into the corresponding component of a dental prosthesis in a casting operation rather than by soldering or with an adhesive. A prefabricated casting core is equally desirable and necessary if the casing is to be made by the establishment or the party who has purchased the core and the corresponding spring (with an integral plunger or with a discrete plunger). All that counts is to provide a kit which can greatly reduce the amount of manual work by a technician so as to ensure that the making of dental prostheses can be simplified and automated as far as possible.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A separable attachment between stationary and removable components of a dental prosthesis, comprising a female detent member in one of the components and a male detent member, said male detent member comprising a flat hollow casing provided in the other component and defining a flat compartment having a width greatly exceeding its height, and an opening communicating with said compartment, a flat elastic spring installed in said compartment and having a width approximating the width of said compartment, and a plunger biased by said spring and normally extending from said casing through said opening under the bias of said spring, said plunger being receivable in the female detent member and the thickness of said spring approximating the height of said compartment.

2. The attachment of claim 1, wherein said plunger contains a metallic material.

3. The attachment of claim 1, wherein said spring contains a rubber-like material.

4. The attachment of claim 3, wherein said material is silicone rubber.

5. The attachment of claim 3, wherein said spring is bonded to said plunger.

6. The attachment of claim 3, wherein said spring substantially fills said compartment.

7. A separable attachment between stationary and removable components of a dental prosthesis, comprising a female detent member in one of the components and a male detent member, said male detent member comprising a hollow casing provided in the other component, defining a compartment and having an opening in communication with said compartment, a spring installed in and occupying a portion of said compartment, a soft mass filling the major part of the remainder of said compartment, and a plunger biased by said spring and normally extending from said casing through said opening under the bias of said spring, said plunger being receivable in the female detent member.

8. The attachment of claim 7, wherein said mass contains rubber.

9. The attachment of claim 8, wherein said mass consists of silicone rubber.

10. The attachment of claim 7, wherein said compartment has a width which greatly exceeds its height, said spring being flat and its width approximating the width of said compartment, the thickness of said spring approximating the height of said compartment.

11. The attachment of claim 10, wherein said spring is embedded in said mass.

12. The attachment of claim 7, wherein said spring, said mass and said plunger substantially fill said compartment so as to reduce the likelihood of growth of bacteria therein.

13. The attachment of claim 7, wherein said plunger is rigid with said spring.

14. A kit for the making of a male detent member for use as a part of a separable attachment between stationary and removable components of a dental prosthesis wherein the male detent member is installed in one of the components and cooperates with a female detent member in the other of the components to separably couple such components to each other, comprising a flat hollow casing defining a flat compartment having a width greatly exceeding its height and an opening communicating with the compartment; a flat spring insertable into said compartment and having a width approximating the width of said compartment, the thickness of said spring approximating the height of said compartment; and a plunger arranged to be biased by said spring upon insertion of the spring into said compartment so that the plunger normally extends from the casing through said opening under the bias of said spring.

15. The kit of claim 14, wherein said plunger is rigid with said spring.

16. The kit of claim 15, wherein said plunger is integral with said spring.

17. The kit of claim 14, wherein said plunger contains a metallic material and said spring contains a rubber-like material.

18. The kit of claim 14, wherein said spring is a serpentine spring.

19. The kit of claim 14, further comprising a common envelope for said casing, said spring and said plunger.

20. The kit of claim 14, further comprising a casting core removably received in said compartment and being replaceable with said spring.

21. An attachment for separably coupling stationary and removable components of a dental prosthesis, particularly a frictional grip slide attachment, comprising a female part arranged to be affixed to one component of the prosthesis; and a complementary male part arranged to be affixed to the other component of the prosthesis, one of said parts having a female detent member and the other of said parts having a male detent member separably connectable with the female detent member to maintain said parts in predetermined positions relative to each other, said male detent member including a flat hollow casing defining a flat compartment having a width greatly exceeding its height and said casing having an opening in communication with said compartment.

22. The attachment of claim 21, further comprisinig a plunger insertable into said compartment, and means for yieldably biasing said plunger, said biasing means being receivable in said compartment inwardly of said plunger and being arranged to bias a portion of said plunger beyond said opening and into said female detent member in said predetermined positions of said parts relative to each other.

23. The attachment of claim 22, wherein said biasing means has a width approximating the width of said compartment and a thickness which approximates the height of said compartment.

* * * * *